(12) United States Patent
Lo et al.

(10) Patent No.: US 10,359,414 B2
(45) Date of Patent: Jul. 23, 2019

(54) FREQUENCY DOMAIN DISCRIMINATION OF TISSUE PROTEINS

(71) Applicant: THE REGENTS OF THE UNIVERSITY OF MICHIGAN, Ann Arbor, MI (US)

(72) Inventors: Joe Fu-Jiou Lo, Westland, MI (US); Zhengtuo Zhao, Dearborn, MI (US); Rui Liu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 692 days.

(21) Appl. No.: 15/064,985

(22) Filed: Mar. 9, 2016

(65) Prior Publication Data

US 2016/0266087 A1     Sep. 15, 2016

Related U.S. Application Data

(60) Provisional application No. 62/130,339, filed on Mar. 9, 2015.

(51) Int. Cl.
*G01C 3/08* (2006.01)
*G01N 33/483* (2006.01)
(Continued)

(52) U.S. Cl.
CPC ........... *G01N 33/4833* (2013.01); *A61B 3/00* (2013.01); *A61B 3/10* (2013.01); *A61B 5/00* (2013.01); *A61B 5/0066* (2013.01); *A61B 5/0071* (2013.01); *A61B 5/0075* (2013.01); *A61B 5/443* (2013.01); *G01N 21/6408* (2013.01);
(Continued)

(58) Field of Classification Search
CPC ........... G01N 33/4833; G01N 21/6408; G01N 21/6486; G01N 2021/6463; G01N 2021/6484; G01N 2201/062; G01N 2201/088; G01N 2333/78; A61B 3/00;
(Continued)

(56) References Cited

U.S. PATENT DOCUMENTS 7,805,183 B2   9/2010   Keely et al.
7,966,060 B2   6/2011   Smit et al.
(Continued)

OTHER PUBLICATIONS

Prabhu, V. et al., "Prognostic prospective of laser induced fluroescence as an objective tool to evaluate collagen deposition in thermal wounds: an ex vivo study." Proc SPIE. Mar. 4, 2014 (8 pages).
(Continued)

*Primary Examiner* — Samantha K Abraham
(74) *Attorney, Agent, or Firm* — Harness, Dickey & Pierce, P.L.C.

(57) ABSTRACT

Devices and methods for performing frequency domain (FD) fluorescence lifetime spectroscopy are provided. The devices include a modulated light source, a focusing optical fiber, a detecting optical fiber, and a detector. The methods include focusing sinusoidal modulated incident light from a light source on a biological sample containing a protein, detecting a range of wavelengths of sinusoidal modulated fluorescent light emitted from the protein, determining a phase shift for the modulated fluorescent light, determining an amplitude modulation of the modulated fluorescent light, and determining a fluorescence lifetime of the protein.

20 Claims, 10 Drawing Sheets

(51) Int. Cl.
G01N 21/64 (2006.01)
A61B 5/00 (2006.01)
A61B 3/00 (2006.01)
A61B 3/10 (2006.01)

(52) U.S. Cl.
CPC . *G01N 21/6486* (2013.01); *G01N 2021/6463* (2013.01); *G01N 2021/6484* (2013.01); *G01N 2201/062* (2013.01); *G01N 2201/088* (2013.01); *G01N 2333/78* (2013.01)

(58) Field of Classification Search
CPC ........... A61B 3/10; A61B 5/00; A61B 5/0066; A61B 5/0071; A61B 5/0075; A61B 5/443
See application file for complete search history.

(56) References Cited

U.S. PATENT DOCUMENTS

| | | | |
|---|---|---|---|
| 8,417,324 | B2 | 4/2013 | Mycek et al. |
| 2007/0197894 | A1 | 8/2007 | Jo et al. |
| 2008/0192262 | A1* | 8/2008 | Enderlein ........... G01N 21/6458 356/610 |
| 2008/0287342 | A1* | 11/2008 | Yu ........................ A61K 38/10 514/1.1 |
| 2012/0326055 | A1* | 12/2012 | Wilson ................. A61B 5/0059 250/459.1 |
| 2013/0149734 | A1 | 6/2013 | Ammar et al. |
| 2015/0104880 | A1* | 4/2015 | Tagawa .............. G01N 21/6486 436/501 |
| 2016/0066833 | A1 | 3/2016 | Yaroslavsky et al. |

OTHER PUBLICATIONS

Luo, T. et al., "Visualization of Collagen Regeneration in Mouse Dorsal Skin Using Second Harmonic Generation Microscopy." Laser Physics, 2009, vol. 19(3), pp. 478-482.

Koehler, M. J. et al., "In vivo assessment of human skin aging by multiphoton laser scanning tomography," Optics Letters 2006, 31(19) p. 2879-81.

Zipfel, W. R. et al., "Live tissue intrinsic emission microscopy using multiphoton-excited native fluorescence and second harmonic generation," PNAS 2003, 100(12) 7075-80.

Zhang, Y. et al., "A compact fiber-optic SHG scanning endomicroscope and its application to visualize cervical remodeling during pregnancy," PNAS 2012 109 (32) 12878-12883.

Brancaleon, L. et al., "In vivo Fluorescence Spectroscopy of Nonmelanoma Skin Cancer," Photochemistry and Photobiology, 2001, 73(2): 178-183 (fluorescence skin cancer detection).

Pu, Y. et al., "Changes of collagen and nicotinamide adenine dinucleotide in human cancerous and normal prostate tissues studied using native fluorescence spectroscopy with selective excitation wavelength." J. Biomed. Opt. 15(4), 047008 (Jul. 23, 2010). doi:10.1117/1.3463479 (5 pages).

Lutz, V. et al., "Characterization of fibrillar collagen types using multi-dimensional multiphoton laser scanning microscopy," International Journal of Cosmetic Science, 2012, 34, 209-215.

Cox, G. et al., "3-Dimensional imaging of collagen using second harmonic generation." Journal of Structural Biology vol. 141, Issue 1, Jan. 2003, pp. 53-62.

Zoumi, A. et al., "Imaging cells and extracellular matrix in vivo by using second-harmonic generation and two-photon excited fluorescence." PNAS, Aug. 2002, 99 (17), pp. 11014-11019, doi: 10.1073/pnas.172368799 (SHG collagen Stronger Than TPE).

Brown, E. et al., "Dynamic imaging of collagen and its modulation in tumors in vivo using second-harmonic generation," Published online: May 18, 2003; doi:10.1038/nm879 Nature Medicine 9, 796-800 (2003) (SHG collagen tumor).

König, K. et al., "Multiphoton autofluorescence imaging of intratissue elastic fibers," Biomaterials vol. 26, Issue 5, Feb. 2005, pp. 495-500 (collagen elastin nadph by SHG).

Ashjian, P. et al., "Noninvasive in Situ Evaluation of Osteogenic Differentiation by Time-Resolved Laser-Induced Fluorescence Spectroscopy," Tissue Engineering vol. 10, No. 3/4, 2004, pp. 411-420.

Marcu, L. et al., "Characterization of Type I, I, I, IV, and V colagens by time-resolved laser-induced fluorescence spectroscopy," Proceedings of SPIE vol. 3917, No. 200 (10 pages).

Elson, D. et al., "Time-domain fluorescence lifetime imaging applied to biological tissue," Photochem. Photobiol. Sci., 2004, 3, 795-801.

Dowling, K. et al., "Fluorescence lifetime imaging with picosecond resolution for biomedical applications," Optics Letters, vol. 23, Issue 10, pp. 810-812 (1998).

Elder, A.D. et al., "Calibration of a wide-field frequency-domain fluorescence lifetime microscopy system using light emitting diodes as light source," J. of Microscopy 2006, 224: p. 166-180.

\* cited by examiner

FREQUENCY DOMAIN DISCRIMINATION OF TISSUE PROTEINS

CROSS-REFERENCE TO RELATED APPLICATIONS

This application claims the benefit of U.S. Provisional Application No. 62/130,339, filed on Mar. 9, 2015. The entire disclosure of the above application is incorporated herein by reference.

FIELD

The present disclosure relates to devices and methods for differentiating proteins by frequency domain fluorescence lifetime spectroscopy.

BACKGROUND

This section provides background information related to the present disclosure which is not necessarily prior art.

Collagen is the main load-bearing structural protein in the extra cellular matrix (ECM) of biological tissue. The quantity, type, and orientation of collagen greatly influences the way tissues carry pressure, stretch, and maintain integrity. For instance, skin wounds transit from weaker type III collagen to type I collagen, improving wound integrity in the later part of healing. Also in the ocular realm, structural composition of type I versus type III collagen varies in different parts of the ocular tissue, which may be linked to diseases such as glaucoma.

Several techniques are currently used to measure tissue collagen compositions, such as histological staining, histological autofluorescence, and non-invasive tissue optical biopsy. Tissue histology provides well-established analysis and quantification methods in techniques such as immunofluorescence and picrosirius staining microscopy. However, histology requires invasive sampling and destructive sectioning to produce samples for measurement.

Alternatively, autofluorescence of collagen can be exploited in various analytical techniques. Autofluorescence from collagen, i.e., without staining, is commonly observed in cell and tissue microscopy. The major collagen fluorophores are lysine derived pyridinium, tyrosine, and phenylalanine groups, which can be affected by crosslinking, glycation, and the overall compositional differences between types of collagens. Collagen autofluorescence, in combination with other endogenous fluorophores, can provide differentiation between normal and cancerous tissues, promising tumor demarcation in minimally invasive surgeries. Moreover, collagen fiber orientation and crystallinity enable second harmonic generation (SHG) using laser induced autofluorescence. Both multiphoton collagen autofluorescence and SHG have been adapted for monitoring skin aging and investigating ocular pathology. Despite the ability of SHG and multiphoton microscopy to detect endogenous fluorophores, e.g., $NADH_+$, elastin, and collagen, no differentiation of collagen types have been demonstrated. This lack of differentiation is because very little differences exist in the spectral domain of collagen types, e.g., I versus III.

However, autofluorescence of different collagen types evidently have strong differences in the time domain—their lifetimes are significantly different and sensitive to the crosslinking and glycation, as mentioned above. Therefore, time domain fluorescence lifetime spectroscopy can provide differentiation of collagen types in tissue. However, laser-induced tissue fluorescence and microscopy techniques have been developed for non-invasive tissue monitoring, but have not enabled differentiation of collagen types specifically. Laser fluorescence and microscopy instrumentation is also prohibitively costly and complicated for widespread biomedical application. Accordingly, there remains a need to develop cost effect and non-invasive methods for measuring tissue collagen compositions.

SUMMARY

This section provides a general summary of the disclosure, and is not a comprehensive disclosure of its full scope or all of its features.

The current technology provides a device or system for measuring an analyte in a biological sample by frequency domain (FD) fluorescence lifetime spectroscopy. The device includes a modulated light emitting diode (LED) source, a first focusing component, a focusing optical fiber, a detecting optical fiber, a second focusing component, and a detector. The first focusing component focuses light from the LED into the focusing optical fiber towards the biological sample, and the detecting optical fiber captures fluorescent light emitted from the analyte in the biological sample and directs the fluorescent light to the second focusing component that focuses the fluorescent light into the avalanche detector.

The current technology also provides a method for detecting a target biological component in a subject. The method includes focusing sinusoidal modulated incident light from a light source on a biological sample containing the target biological component, detecting a range of wavelengths of sinusoidal modulated fluorescent light emitted from the biological component when present in the biological sample; determining a phase shift for the modulated fluorescent light, determining an amplitude modulation for the modulated fluorescent light, and determining a fluorescence lifetime of the biological component, to thereby detect the presence or quantity of the biological component.

Additionally, the current technology provides a method for detecting collagen in a biological sample. The method includes focusing incident light with a wavelength of from about 350 nm to about 375 nm and a sinusoidal modulated intensity of from about 40 MHz to about 60 MHz from a modulated light emitting diode (LED) on the biological sample, detecting a range of sinusoidal fluorescent light emitted from collagen within the biological sample, determining at least one phase shift value and at least one amplitude suppression value for the range of sinusoidal fluorescent light, fitting the at least one phase shift value and the at least one amplitude suppression value into a multi-exponential decay model, and determining a fluorescence lifetime of the collagen, so as to detect the collagen or measure the quantity of collagen in the biological sample.

Additionally, the current technology provides a method for detecting a combination of tissue structural proteins in a biological sample. The method includes detecting a range of sinusoidal fluorescent light emitted from the combination of tissue structural proteins when present in the biological sample, determining at least one phase shift value and at least one amplitude suppression value for the range of sinusoidal fluorescent light emitted from the tissue structural proteins, fitting the at least one phase shift value and at least one amplitude suppression value for the range of sinusoidal fluorescent light emitted from the tissue structural proteins into a multi-exponential decay model; and determining fluorescence lifetimes of the combination of tissue structural proteins so as to detect their relative quantities in the biological sample. Detecting a range of sinusoidal fluorescent light emitted from the combination of tissue structural proteins when present in the biological sample may include detecting a range of sinusoidal fluorescent light emitted from each of the tissue structural proteins. In various embodiments, the tissue structural proteins include type I collagen, type III collagen, and elastin. Moreover, the method may also include comparing the fluorescence lifetime of the elastin to the fluorescence lifetimes of the type I collagen and type III collagen and determining a quantity of the elastin relative to the type I collagen and type III collagen.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 7A:
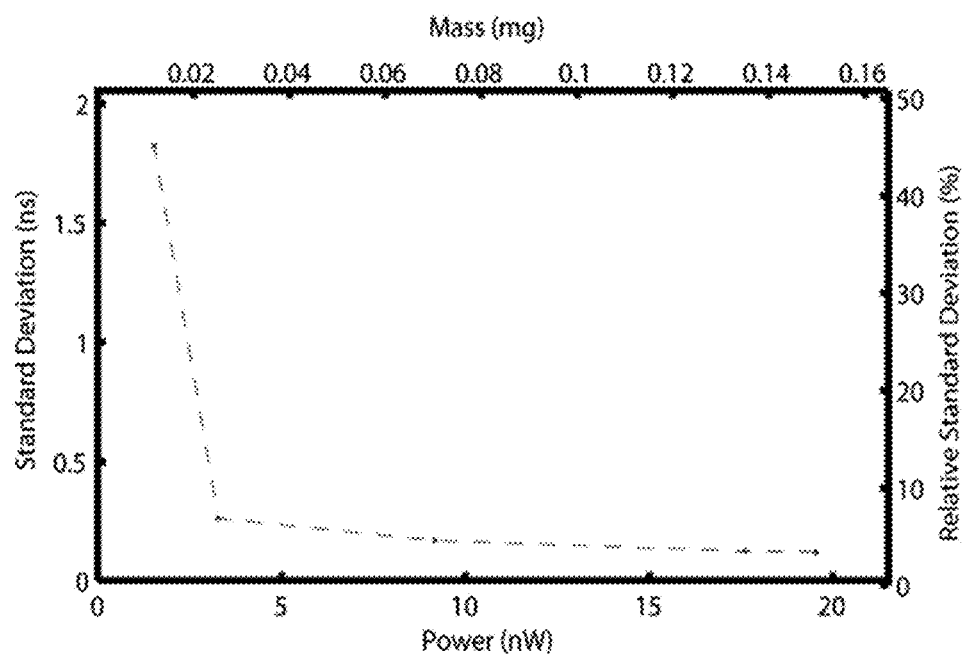
Figure 7B:
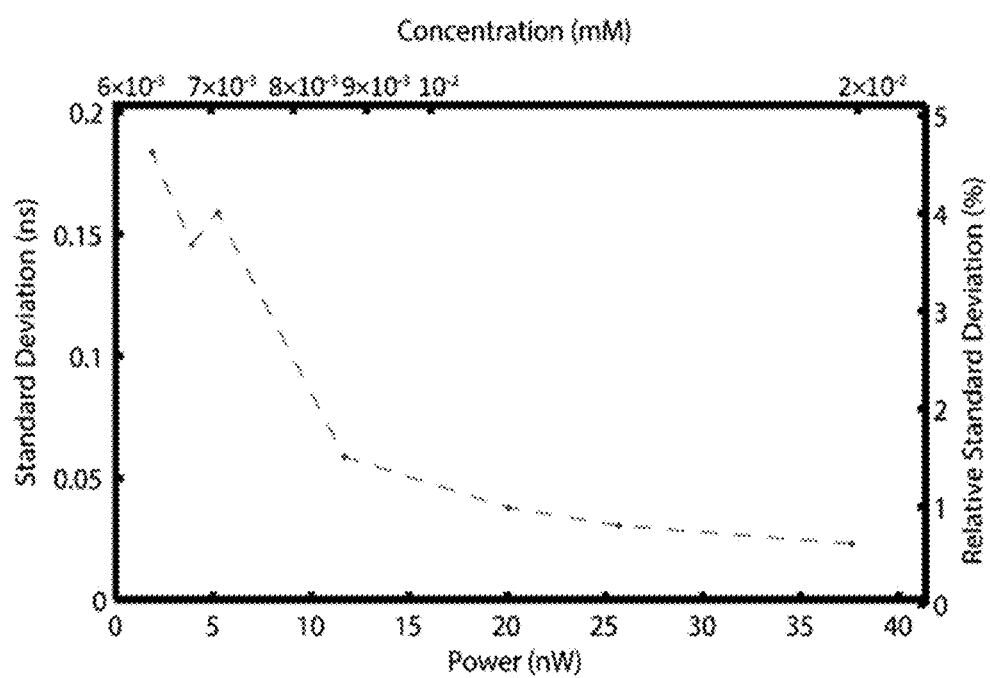

FIG. 7A is a graph showing sensitivity of solid samples characterized by using collagen I detections at various masses, with the resultant time resolution (in ns) and relative standard deviations plotted against power and mass; and FIG. 7B is a graph showing sensitivity of liquid samples characterized by using FAD detection at various concentrations, with the resultant time resolution and relative standard deviations plotted against power and concentrations.

Corresponding reference numerals indicate corresponding parts throughout the several views of the drawings.

DETAILED DESCRIPTION

Example embodiments will now be described more fully with reference to the accompanying drawings.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Figure 1A:
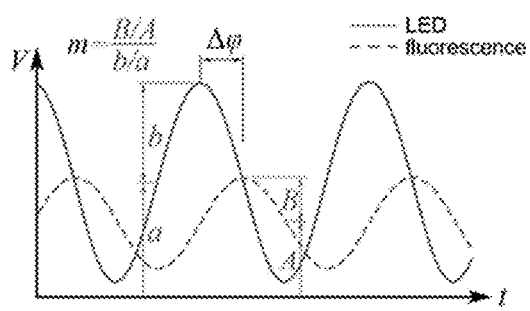
FIG. 1A shows a frequency domain fluorescence lifetime, which is based on a phase shift and demodulation of fluorescence emission excited by a modulated light source.

To study the effects of collagen composition in tissues, a non-invasive, type I and type III specific detection technique is required. Therefore, the present technology provides a low cost, low complexity light emitting diode (LED) based system to realize both non-invasive detection and specific discrimination of collagen variations in tissue. In addition, elastin, another important ECM protein, is also included as a comparison. In general, modulated LED intensity is applied in order to calculate tissue autofluorescence lifetimes based on frequency domain (FD) fluorescence lifetime spectroscopy, as shown in FIG. 1A. Specifically, FIG. 1A is a graph that shows that frequency domain fluorescence lifetime is based on a phase shift and amplitude demodulation of fluorescence emission excited by a modulated light source. Using this method, fluorescence lifetimes from collagen type I versus type III and elastin can be clearly distinguished. Due to the low cost of LED and photodiode components, low complexity of fiber optic probes, and the possibility to integrate phase and demodulation analysis on an integrated circuit (IC), FD collagen technique is well suited for portable applications. Applications in implantable sensors, field diagnostics, and clinical monitoring can benefit from the technique to determine collagen and elastin distributions in biological tissues over time.

Collagen autofluorescence, and fluorescence in general, can be modeled as a linear, time-invariant system with a characteristic impulse response function specific to a particular fluorophore. Therefore, the input (excitation) and output (emission) of such a system can be considered in time and frequency domains. In the time domain, the input excitation is convolved with the impulse response to yield the emission intensity over time. This time domain method has been demonstrated with sub-nanosecond pulsed lasers and fast photomultiplier tube (PMT) detectors to reconstruct collagen fluorescence impulse response decays, with associated lifetime constants. While the time domain method provides significant information over shorter pulses, the cost of the pulsed lasers, triggering electronics, and PMT detectors, in addition to the complexity of the system, prevent its wider use in biomedical applications. On the other hand, the frequency domain method provided herein is a linear time-invariant system that applies a sinusoidal modulation to excitation intensity, resulting in a sinusoidal emission with amplitude suppression and phase shift. The frequency domain lifetime method is a cost-effective alternative to monitoring biological tissues. Optimum modulation frequencies for tissue fluorophores, e.g., collagen, elastin, and NADH, range from about 10 MHz to about 100 MHz, lowering the requirements for the LED modulation electronics, photodetector temporal response, as well as signal digitization and recording speed. Moreover, a single multi-channel oscilloscope can perform the timing and acquisitions for both the excitation and emissions signals. Using the phase ($\Delta\phi$) and demodulation (m) from oscilloscope measurements, two lifetimes, $\tau_\phi = \omega^{-1} \tan \Delta\phi$ and $\tau_m = \omega^{-1}(m^{-1}-1)^{1/2}$, can be calculated and combined via multi-exponential models to find characteristic lifetimes of a sample. In various aspects of the present technology, the characteristic lifetimes of fluorescence standards, purified collagen proteins, and ocular and skin tissue samples are measured to demonstrate the utility of the frequency domain lifetime method.

Figure 1B:
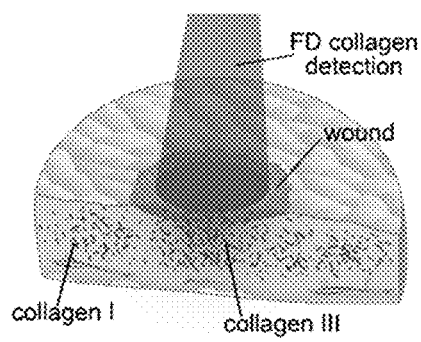
FIG. 1B is a schematic illustration of non-contact monitoring of wound healing.

As shown in FIG. 1B, skin wounds provide a model to demonstrate the current technology because they transit from weaker type III collagen to type I collagen, improving wound integrity in the later stage of healing.

Figure 1C:
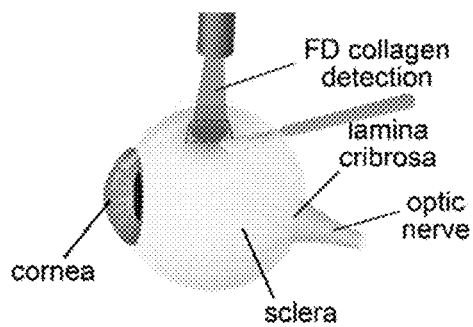
FIG. 1C is a schematic illustration of non-invasive probing of ocular tissue.

As shown in FIG. 1C, ocular tissues also provide a model to demonstrate the current technology because the type and orientation of collagen fibers vary by region in the eye and are closely related to its function. Eye tissue represents a challenge to the measurement technique because sclera (human) contains about 90% type I collagen and less than 5% type III collagen. Levels of type III collagen in the bovine cornea averages less than 1% in animals older than 3 months. Type III collagen is important to the eye's function, but its comparatively low levels in eye tissue complicate the ability of a detection system to discern it. Bovine tissue is analyzed herein because it is of similar consistency to human eye tissue and is often used as a precursor to experiments using cadaveric or surgical specimens of human origin.

The relation between an eye's collagen composition, its function and various diseases such as glaucoma and keratoconus, is important due to various relative correlations. Similar to other connective tissues, sclera is primarily composed of a matrix containing collagens, elastin and proteoglycans, resulting in viscoelastic properties that help to protect the eye from injury during brief elevations in intraocular pressure due to eye movements and other events such as rubbing. In the cornea, the lamellae are composed of collagen fibrils of uniform diameter running parallel to one another; however, in the sclera the lamellae are composed of collagen fibrils of varying diameter with an irregular branching pattern. The direction of collagen fiber orientation varies with location in the sclera, with more circumferential alignment in the peripapillary region. There appear to be significantly fewer fibers oriented in the direction through the wall's thickness than there are in-plane. The fibrils are primarily composed of type I collagen, although types III, IV, V, VI, VIII, XII and XIII have also been identified to a lesser extent. The non-collagen components of scleral matrix include elastin, which forms fibrils that reinforce the collagen framework.

Systems

Figure 2:
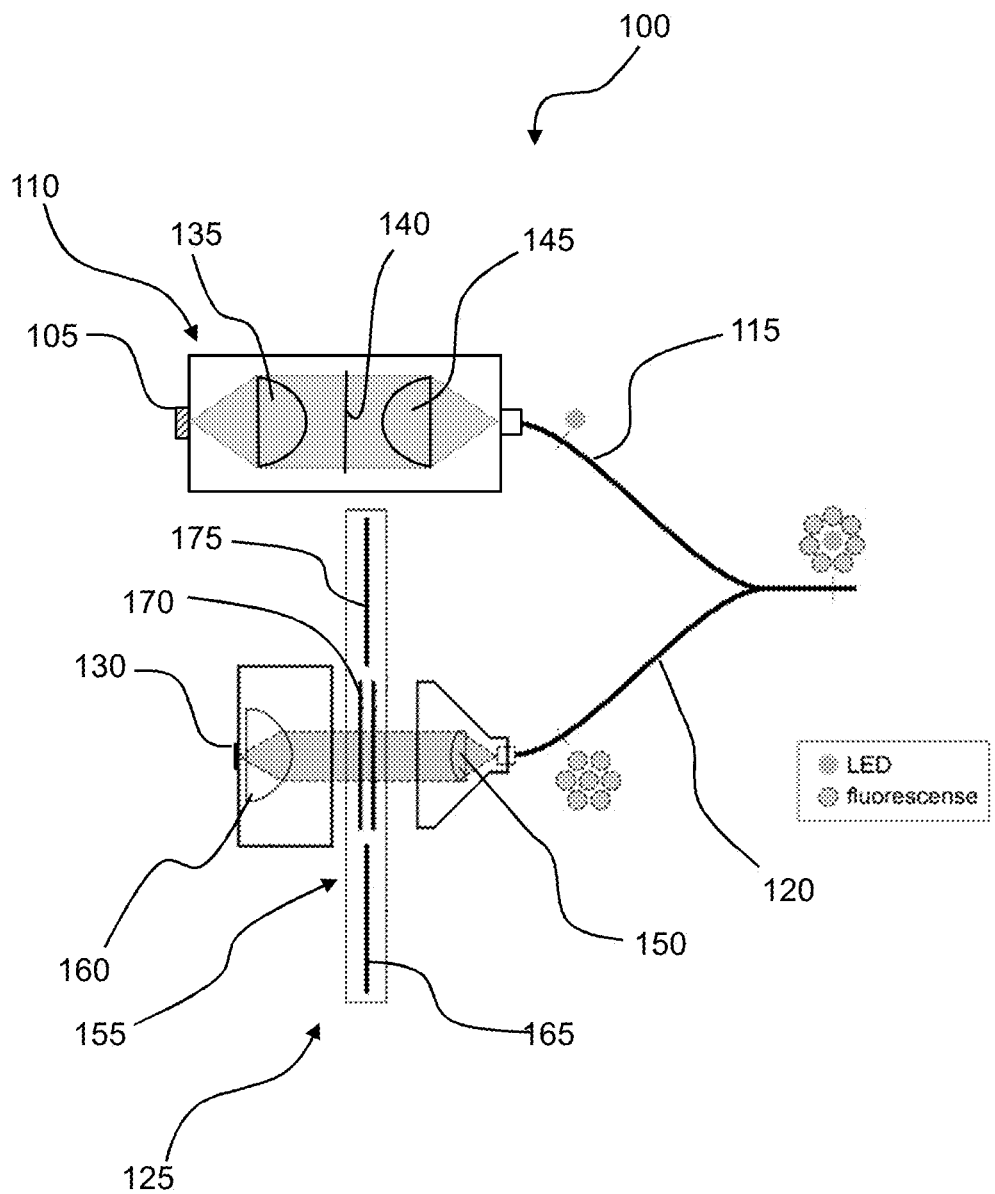
FIG. 2 is a schematic illustration of a frequency domain fluorescence lifetime system according to the present technology.

With reference to FIG. 2, the present technology provides a device or system 100 for measuring an analyte in a biological sample by frequency domain fluorescence lifetime spectroscopy. In various embodiments, the analyte is a protein that exhibits autofluorescence. Non-limiting examples of such proteins include collagen type I, collagen type III, elastin, nicotinamide adenine dinucleotide (NADH), phenols, tryptophans, flavins, glycation adducts, and combinations thereof. The biological sample is a biological tissue, such as a biopsy specimen or a tissue on a human or non-human mammalian subject. In some embodiments, the biological sample is skin, a wound located on a subject's skin, or an eye. Due to the non-invasive nature of the methods afforded by the device 100, analytes can be measured without general or local anesthetics.

The device 100 comprises a modulated light source 105, a first focusing component 110, a focusing optical fiber 115, a detecting optical fiber 120, a second focusing component 125, and a detector 130.

The modulated light source 105 is any modulated light source known in the art. However, in some embodiments, the first light source 105 is an intensity-modulated LED. The LED can emit light with a wavelength from about 300 nm to about 750 nm. Therefore, the LED can emit ultraviolet (UV) light, near UV light, visible light, near infrared (IR) light, or IR light. In various embodiments, the LED emits UV light or light with a wavelength from about 350 nm to about 375 nm. The intensity modulation is sinusoidal from about 1 MHz to about 100 MHz. As used herein, the term "sinusoidal" means that a variable or characteristic, such as, for example, intensity, is continuously changed from a first value to a second value, back to the first value, and so on over time with a predictable function equal and opposite of its second derivative, e.g., a sine curve. In one embodiment, the LED has a sinusoidal modulated intensity of from about 40 MHz to about 60 MHz.

The first focusing component 110 focuses light from the light source 105 to the focusing optical fiber 115. The first focusing component 125 comprises a first lens 135, a first filter 140, and a second lens 145, wherein the filter 140 is located between the first lens 135 and the second lens 145. The first filter 140 is dependent on the wavelength of light emitted by the light source 105. As a non-limiting example, where the light source emits light with a wavelength of about 365 nm, the first filter 140 may be a 375 low-pass filter or a 275-375 nm bandpass filter.

In various embodiments, the first and second lenses 135, 145 are plano convex lenses. However, the first and second lenses 135, 145 can be any appropriate lenses known in the art. The first focusing component 125 focuses light from the light source 105 to the focusing optical fiber 115. Specifically, the first lens 135 directs light from the light source 105 through the first filter 140. The light then contacts the second lens 145, which directs the light to the focusing optical fiber. In various aspects, the light can be focused onto a biological sample with a probe (a probe tip is shown with 8 circles/fibers). The probe can also capture fluorescent light emitted from an analyte within the sample.

Fluorescent light emitted from an analyte is captured by the detecting optical fiber 120. In various embodiments, the device 100 comprises a plurality of detecting optical fibers 120. For example, the device 100 can comprise one optical fiber, at least one optical fiber, or from 1 to about 20 optical fibers 120. The device 100 shown in FIG. 2 comprises 7 detecting optical fibers 120. The second focusing component 125 captures light from the detecting optical fiber 120 and focuses the light on a detector 130. Specifically, the second focusing component 125 comprises a third lens 150, a filter component 155, and a fourth lens 160, wherein the filter component 155 is positioned between the third lens 150 and the fourth lens 160. In various embodiments, the third lens 150 is a plano convex lens and the fourth lens 160 is an aspherical lens. However, the third and fourth lenses 150, 160 can be any appropriate lenses known in the art.

The filter component 155 comprises a second filter or a plurality of second filters. As shown in FIG. 2, the filter component 155 comprises a second filter 165, a third filter 170, and fourth filter 175, which are interchangeable, for example, by use of a filter wheel. In other words, the second filter is selected from the group consisting of a second filter 165, a third filter 175, or a fourth filter 175. In one embodiment, the device 100 comprises two third filters 170. As non-limiting examples, the second filter 165, the third filter 170, and the fourth filter 175 can be a neutral density filter, a pair of 400 nm high pass filters, and a pin hole filter, respectively. The second focusing component 125 focuses fluorescent light emitted from the analyte and transported by the detecting optical fiber 120 through the third lens 150, through the second filter in the filter component 155, through the fourth lens 160, and to the detector 130.

The detector 130 can be any detector known in the art. As non-limiting examples, the detector 130 can be an avalanche detector, a complementary metal-oxide semiconductor (CMOS) detector, or a photomultiplier tube (PMT). In various embodiments, the detector 130 is an avalanche detector.

Methods

The present technology provides methods for detecting or measuring a biological component or target analyte, such as a protein, or a combination of a plurality of tissue structural proteins, in a subject. More particularly, the present technology provides a method of performing FD fluorescence lifetime spectroscopy to detect, analyze, and measure biological components in a subject. For example, the methods can be performed to detect or measure the presence and/or quantity of a target analyte, the presence and/or quantity of at least one target analyte or the relative quantities of more than one target analyte in a biological sample. The methods are performed with the device or system describe above. The biological component can be any biological component known in the art, including a combination of components, such as a combination or plurality of tissue structural proteins. Non-limiting examples of biological components include proteins, such as type I collagen, type III collagen, and elastin. The biological component is located in a biological sample. In various embodiments, the methods are non-invasive. Therefore, for non-invasive methods, the biological sample can be the skin of a subject, a wound on a subject, a subject's eye, or any other abnormality present on a subject that is accessible by non-invasive means. As used herein, "non-invasive means" are means that do not physically damage, chemically alter, infiltrate, or destroy tissue, such as skin. As used herein, the subject can be any human or non-human subject, including non-human mammals.

The method comprises focusing a sinusoidal modulated incident light from a light source on a biological sample comprising the biological component. The incident light is light emitted from a light source, such as the light sources described above. In various embodiments, the light source is a modulated LED. The wavelength of the light is a wavelength that is sufficient to be absorbed by a desired biological component, which then emits light as fluorescence. In many embodiments, the light is in the UV region of the spectrum. Additionally, the intensity of the light is modulated at from greater than or equal to about 10 MHz to less than or equal to about 100 MHz, or from a range therein, including from greater than or equal about 40 MHz to less than or equal to about 60 MHz. When the biological component or analyte is type I collagen, type II collagen, or elastin, the method comprises focusing sinusoidal modulated incident light from a light source comprises focusing light with a wavelength of about 365 nm from a light emitting diode (LED) with a sinusoidal modulated intensity of from greater than or equal to about 10 MHz to less than or equal to about 100 MHz. Additionally, filters can be used to filter out undesired wavelengths of light that may interfere with FD fluorescence lifetime spectroscopy.

The incident light is focused upon a biological sample where the light is absorbed by the target biological component. It is understood that the target biological component can be more than one biological component, such as, for example, a component selected from the group consisting of type I collagen, type III collagen, elastin, and combinations thereof. The biological component thereby emits light as fluorescence, which is captured by a detecting optical fiber and directed or transferred to a detector. Thus, the current method further comprises detecting a range of wavelengths of sinusoidal modulated light ("fluorescent light") emitted from a target biological component when present in the biological sample. Detecting can be performed by any method known in the art, including by the devices described herein. Therefore, the method includes acquiring data for determining at least one phase shift for the modulated fluorescent light and for determining at least one amplitude difference or modulation of the modulated fluorescent light. Then, the method comprises determining a fluorescence lifetime of the biological component from the at least one phase shift value and from the at least one amplitude modulation, so as to detect the presence or quantity of the biological component or the relative quantify of the biological component in relation to another component. Methods for calculating phase shifts, amplitude modulations and lifetimes are described in detail below.

Embodiments of the present technology are further illustrated through the following non-limiting example.

Example

Changes in the composition of type I and type III collagen in tissue can shed light on various diseases. However, the majority of current collagen detection techniques require invasive and destructive tissue sampling. Here, a low cost, low complexity light emitting diode (LED) based system is developed to realize both non-invasive detection and specific discrimination of collagen variations in tissue. Modulated LED intensity has been applied to calculate tissue autofluorescence lifetimes based on frequency domain (FD) fluorescence lifetime spectroscopy. Using this method, fluorescence lifetimes from collagen type I versus type III is clearly separated at 3.94 ns and 5.01 ns, respectively, distinct from the elastin lifetime at 6.78 ns. The probe is tested on cow ocular tissues, with cornea showing much shorter average lifetimes of 4.27 ns than sclera at 7.48 ns. Furthermore, measurements of an 8 mm murine skin wound at 14 days post-wounding also show distinct, longer average lifetimes at 9.74 ns versus normal skin at 6.72 ns. This FD collagen detection can examine through tissue structures and discern the underlying pathology nondestructively.

FD Collagen System Overview

An FD Collagen system is composed of the following components: A modulated 365 nm wavelength LED (DC3100-365, Thorlabs, NJ) used as the light source along with a 375 nm low-pass filter. This sinusoid modulated excitation light is carried by a 7 around 1 UV-resistant fiber probe (Stellarnet, FL) to illuminate a sample at frequencies from greater than or equal to about 10 MHz to less than or equal to about 60 MHz. Emission and reflected/scattered light from the sample are collected by the 7 fibers and the reflected light is then filtered by two 400 nm high pass emission filters. An avalanche photodiode (APD; APD-110C, Thorloabs, NJ) picks up the filtered emission intensity and compares its modulation to the LED source on an oscilloscope (see FIG. 2). Because of the availability of modulated LED, fast avalanche photodiode, and sub 100 MHz oscilloscope at affordable costs, the FD Collagen system does not require an extra signal generator or heterodyne electronics, and has a generally low overall system cost.

System Optomechanics

To couple the light from the LED to the filter probe, a plano convex lens (φ25.4, f=25.4) is used to collimate the light through the 375 nm low pass filter, which is then focused by a second plano convex lens (φ25.4, f=25.4) onto the fiber probe. The fiber probe configuration has one illumination core in the center and 7 surrounding collection cores. This configuration gives high collection efficiency with small detection spot provided by the single illumination core. Similar to the LED coupling, detector coupling is achieved by collimating the collection fiber output through high pass emission filters. Then, a signal, i.e., fluorescent light emitted from collagen, is focused on the APD with a plano convex lens (φ12.7, f=20.0) and an aspherical lens (φ25.0, f=20.0). Moreover, high pass emission filters, as well as neutral density filters, are mounted on a filter wheel to enable them to be moved in and out of the light path during normal and calibration operations.

System Calibration

Phase shift and modulation depth ratio of the system are calibrated for comparisons between solid and liquid sample calibration measurements. During these calibration measurements, the emission filters are switched out and replaced with neutral density filters or pin holes to further reduce intensity. For reference phase angles, reflected light is measured at 10 to 60 MHz from frosted glass, scattering in water, and scattering in ethanol to compare to measurements from powder/fiber form, aqueous solutions and ethanol solutions, respectively. For the reference modulation depth ratios, the LED waveform's b/a ratios are measured for the frosted glass, water, and ethanol solutions, to parallel those measured for phase references.

Fluorescence Standard, Purified Protein, and Tissue Sample Preparation

For comparison to known lifetime standards, three fluorescence standards are measured: flavin adenine dinucleotide (FAD), fluorescein, and 9-Anthracenecarboxylic acid (9CA). 0.1 mM FAD is prepared in water while 0.1 mM fluorescein and 9CA are prepared in ethanol. FAD, fluorescein, and 9CA have lifetimes of 2.57, 3.94, and 11.75 ns, respectively, covering the range of lifetimes expected from purified ECM proteins. Then, three purified ECM proteins are measured, collagen I, collagen III, and elastin, to represent important ECM components in ocular and skin tissues. Purified proteins are measured in solid powder or fiber forms. Finally, ex-vivo lifetime measurements are conducted in bovine sclera and cornea tissues, and murine normal and wound skin tissues (14 days post-wounding).

Bovine eyes are obtained from a local slaughterhouse and tested within 48 hours of the donating animal's death. Scleral and corneal tissues are dissected from the surrounding fat and extraocular muscles of the eye, then separated from the internal contents of the eye. These tissues are then cut into 1 mm squares for measurement. Measurements are done normal to the external surface of the ocular tissues.

All animal procedures followed University of Illinois guidelines for the humane treatment of animals and are approved by the University of Illinois Institutional Animal Care and Use Committee. BALB/C mice were used in the skin wound model. Wound models are created using 5 mm punch biopsies on day 0 and collecting on day 14 post-wounding with 8 mm punch biopsies. Immediately after biopsy sampling, skin and wound tissues are measured normal to the external surface of the tissues.

Data Analysis

During data acquisition, raw emission signals are averaged 128 times in the oscilloscope to reduce effects of noise. Then, the averaged signals are imported into Matlab (Math Works, Inc.) and fitted to sine functions. The least-square method is employed to fit the raw signals to sine function with known frequency.

$$y = a\sin(\omega x - \phi) + b, \text{ or } y = A\sin(\omega x - \phi) + B \quad (1)$$

Here, $\omega$ is known when the sample is excited under the LED light with a certain frequency, x is the time axle, and y is the raw data. Parameters phase $\phi$, amplitude a, offset b for the excitation and phase $\phi$, amplitude A, offset B for the emission waveforms (see FIG. 1A) are readily extracted from the curve fit. However, there are noticeable DC offsets in the raw signals depending on measurement frequency and oscilloscope settings. Therefore, DC offsets from dark readings (LED turned off) at specific measurement conditions are subtracted from the raw data before fitting and data processing. This process allows more accurate calculations of the phase shift angles and modulation depths, without peak uncertainties, amplitude drifts, and waveform asymmetries from one part of the raw data to another, leading to better lifetime measurements.

After getting the phase angles and modulation depth ratios between 10 MHz to 60 MHz, the data is fitted to a multi-exponential model, where the fluorescence impulse response function is assumed to be:

$$I(t) = \Sigma_{i=1}^{n} \alpha_i e^{-t/\tau_i} \quad (2)$$

Here, $\alpha_i$ is the lifetime fraction of each component $\tau_i$ and $\Sigma \alpha_i = 1 = 1$. Thus I(t) appears as a decay curve containing multiple exponents represented in the sample. The calculated phase shift angle $\phi_{c\omega}$ and modulation $m_{c\omega}$ can then be obtained from the sine $N_\omega$ and cosine $D_\omega$ transformation of I(t):

$$N_\omega = \frac{\int_0^\infty I(t)\sin \omega t\, dt}{\int_0^\infty I(t)\, dt} \quad (3)$$

$$D_\omega = \frac{\int_0^\infty I(t)\cos \omega t\, dt}{\int_0^\infty I(t)\, dt} \quad (4)$$

where their numerical values can be calculated by:

$$N_\omega \cdot J = \sum_{i=1}^{n} \frac{\alpha_i \omega \tau_i^2}{1 + \omega^2 \tau_i^2} \quad (5)$$

$$D_\omega \cdot J = \sum_{i=1}^{n} \frac{\alpha_i \tau_i}{1 + \omega^2 \tau_i^2} \quad (6)$$

where $J = \Sigma \alpha_i \tau_i$.

Thus the phase shift angle $\phi_{c\omega}$ and modulation $m_{c\omega}$ are described by:

$$\phi_{c\omega} = \arctan(N_\omega/D_\omega) \quad (7), \text{ and}$$

$$m_{c\omega} = (N_\omega^2 + D_\omega^2)^{1/2} \quad (8).$$

An error-weighted $\chi^2$ sum of the squares of the deviations between the measured and calculated values is minimized to find the best fitting of multi-exponential model.

$$\chi^2 = \sum_\omega \frac{1}{\sigma_\phi^2}(\phi_\omega - \phi_{c\omega})^2 + \sum_\omega \frac{1}{\sigma_m^2}(m_\omega - m_{c\omega})^2 \quad (9)$$

Here, $\sigma_\phi$ and $\sigma_m$ are the typical uncertainties in the phase and modulation data, respectively. Respective standard deviations from their measurements are used to represent these uncertainties. A single exponential model is used for fluorescence standard FAD, fluorescein, and 9CA, to be consistent with other reported studies. A two-exponential model is used for protein and tissue samples, where fractional $\alpha_1$, $\alpha_2$, and their respective $\tau_1$ and $\tau_2$ are calculated by minimizing the $\chi^2$ function describing deviations of their $\phi\omega$ and $m_\omega$ values.

Statistical Analysis

Three readings (n=3) of each group of data are used for statistical analysis of the collagen proteins, ocular tissues, and skin wound samples. Individual analyses of variance (ANOVA) were performed first to assess the group difference. Post hoc pairwise comparisons by individual-samples t-test (single sided) are then examined. Note that multiple comparisons adjustments are not performed for these analyses, but the p-values and 95% confidence intervals (CI) are provided for interpretation.

Results and Discussion

To characterize the FD collagen system, the calibration results and fluorescence spectra of each standard, protein, and tissue samples are presented. Then, the FD phase shift and demodulation results are presented. Next, the single and multi-exponential fitted lifetimes are summarized in Tabulated form. Finally, the relationship between temporal resolution and sample detectivity is characterized to describe the sensitivity of the FD system.

System Calibration Results

Figure 3A:
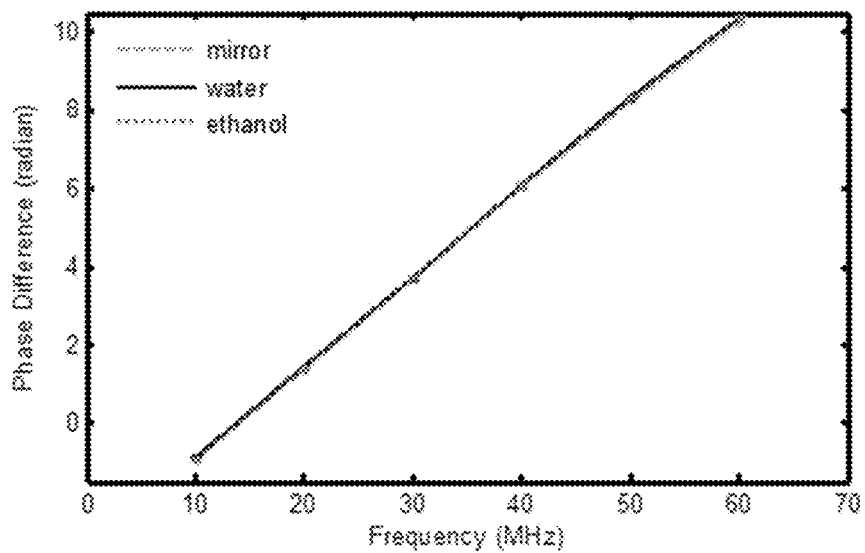
FIG. 3A is a graph showing phase delays versus frequency of LED modulation, wherein measurements are made using mirror/water/ethanol references to represent solid, aqueous, and ethanol solvated samples.
Figure 3B:
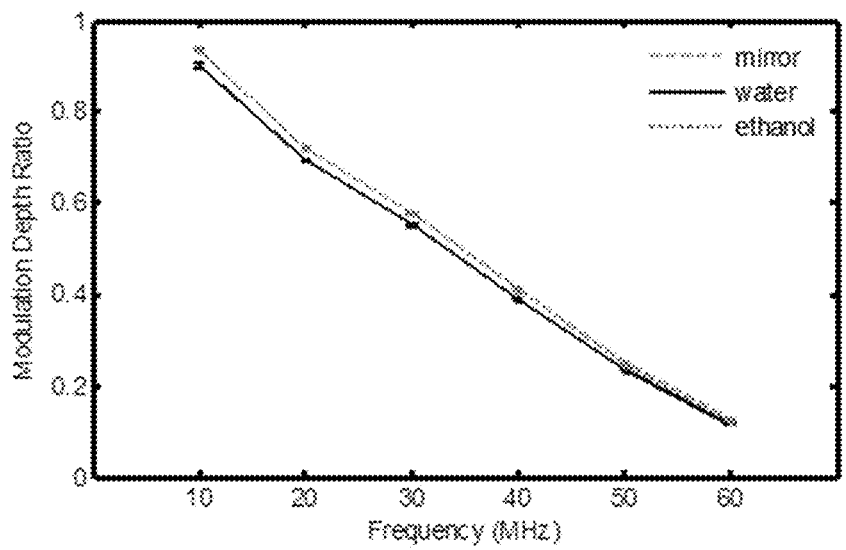
FIG. 3B is a graph showing modulation ratios versus frequency of LED modulation, wherein measurements are made using mirror/water/ethanol references to represent solid, aqueous, and ethanol solvated samples.

The phase angles of mirror/water/ethanol references are fairly close to each other, as shown in FIG. 3A. As with phase references, modulation references did not change significantly among all samples, as shown in FIG. 3B.

Spectral Domain Alone Cannot Distinguish Collagen Types

Figure 4A:
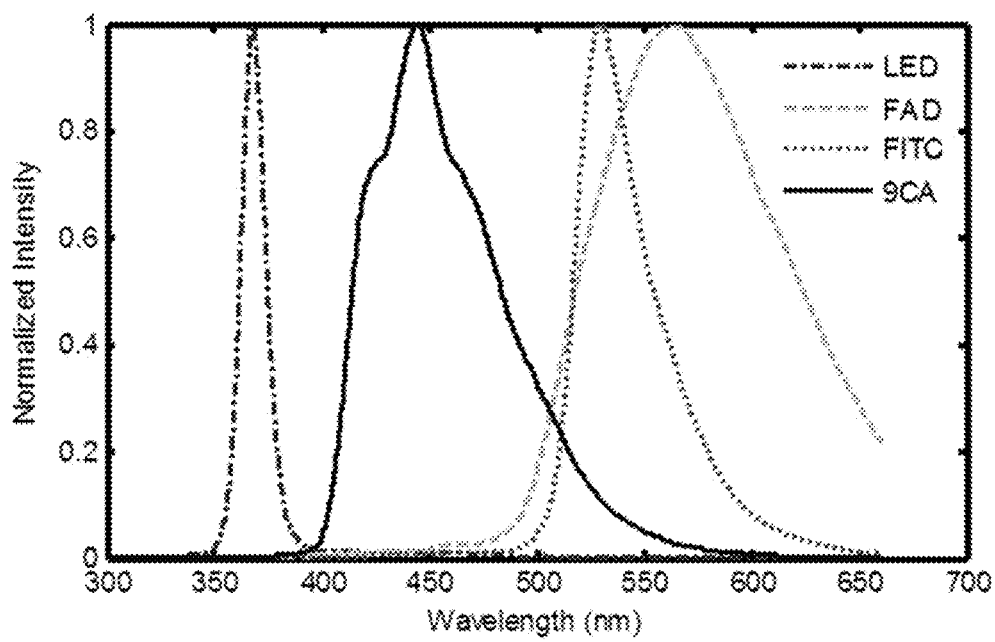
FIG. 4A is a graph showing emission spectra of standards shown with LED excitation spectra overlaid, wherein the standards were in 0.1 mM concentration in their respective solvents.
Figure 4B:
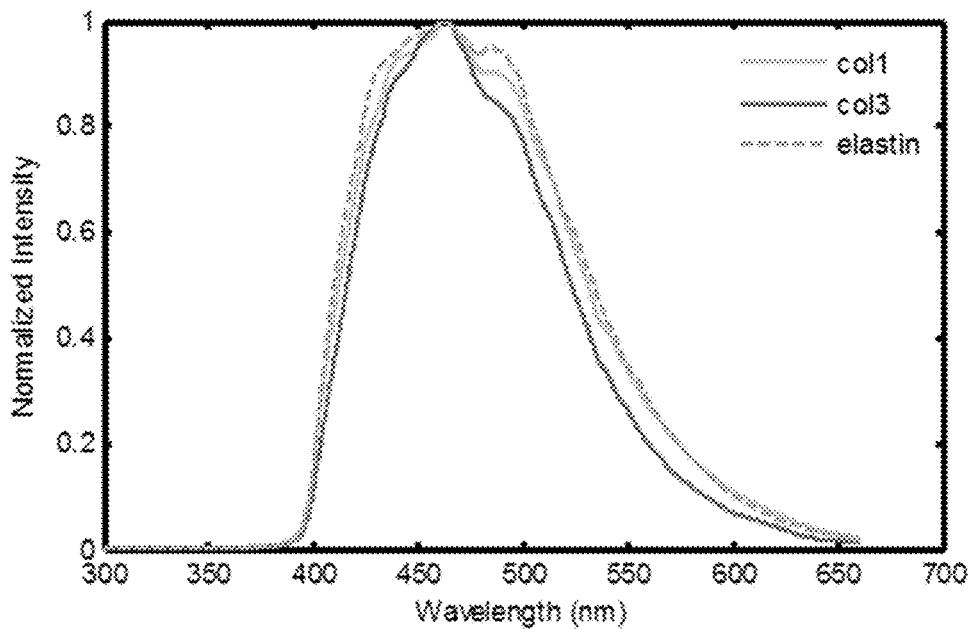
FIG. 4B is a graph showing emission spectra of purified protein samples, wherein the proteins are in powder/fiber forms.
Figure 4C:
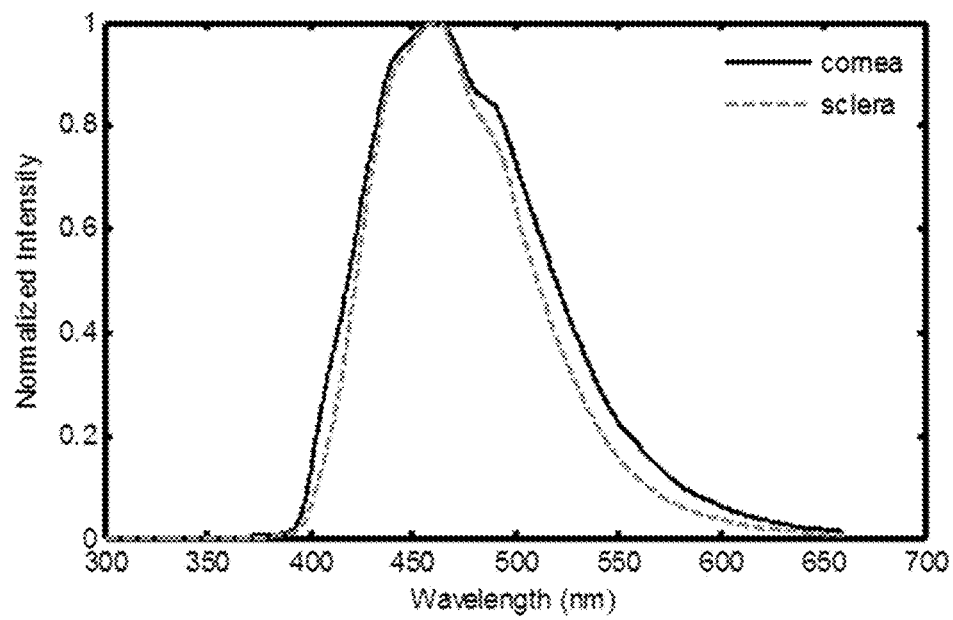
FIG. 4C is a graph showing emission spectra of ocular tissues samples.
Figure 4D:
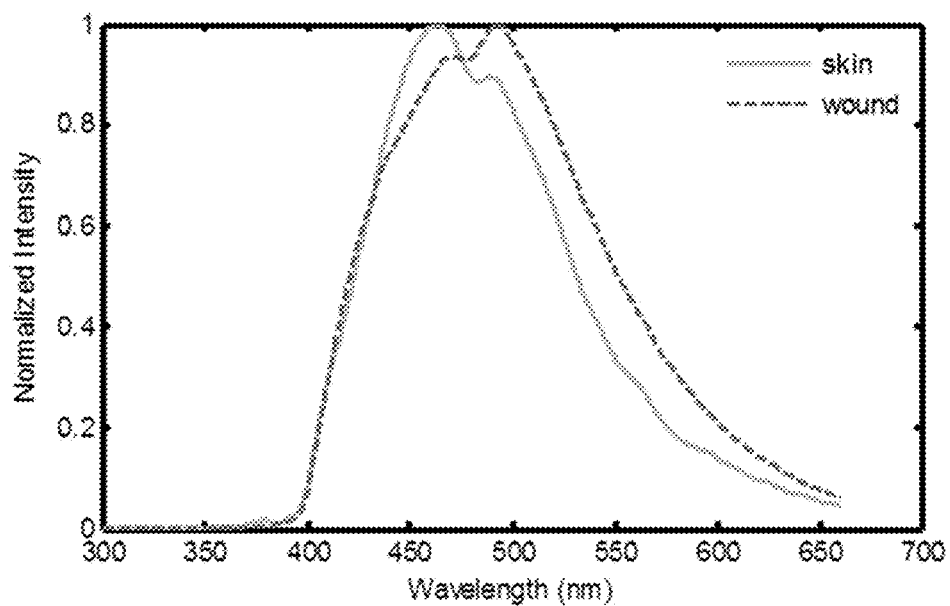
FIG. 4D is a graph showing emission spectra of skin and wound tissue samples that indicate that skin and wound tissue samples have a significant overlap in intensity above 450 nm due to multiple protein compositions.

Spectral data shown in FIG. 4A show a 9CA peak at 450 nm, a fluorescein peak at 520 nm, and a FAD peak at 530 nm. As shown in FIG. 4B, protein spectra generally overlap for collagen I/III and elastin, but show significant intensity differences above 450 nm. This spectral overlap, combined with other present chromophores like hemoglobin, makes tissue autofluorescence complicated and difficult to interpret. With reference to FIG. 4C there is spectral overlap between cornea and sclera. With reference to FIG. 4D, there is some overlap between skin and wound, but skin and wound have a significantly difference in the intensity above 450 nm that is complicated by multiple protein compositions. In the current FD Collagen system, lifetime measurements are employed to distinguish purified protein components by integrating all wavelengths above 400 nm.

Frequency Domain Phase Shift Results

Figure 5A:
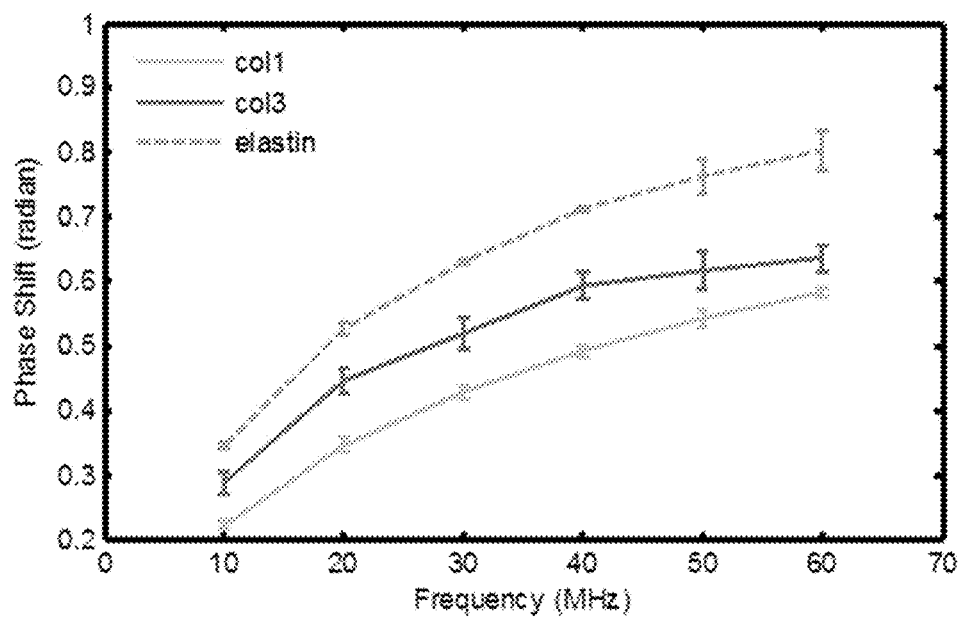
FIG. 5A is a graph showing fluorescence standards with increasing phase shift between FAD, fluorescein, and 9CA, as expected by the order of their increasing lifetimes, wherein error bars denote standard deviations.
Figure 5B:
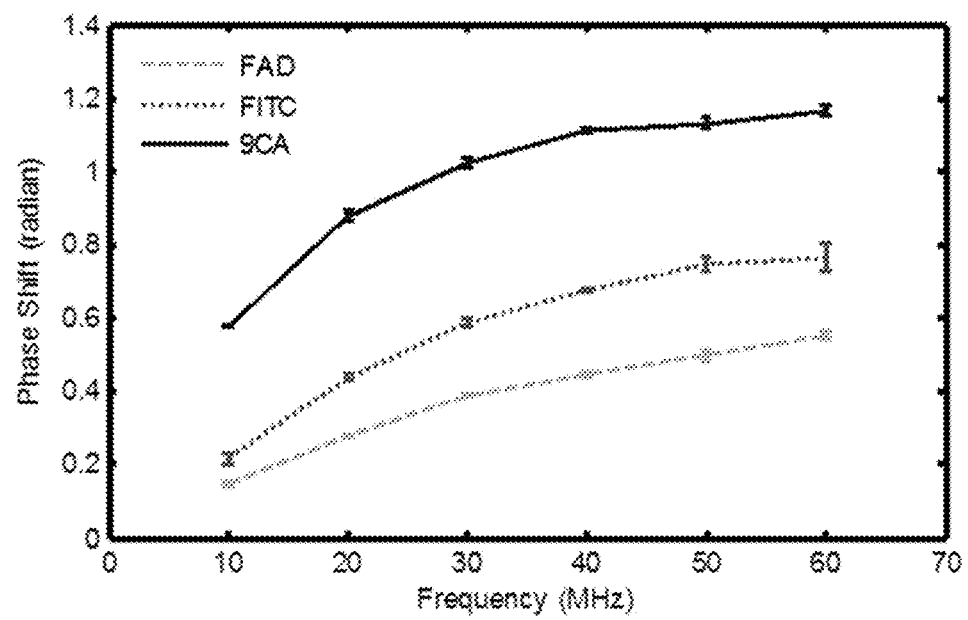
FIG. 5B is a graph showing that phase shifts between type I and III collagen are distinct, *$p<0.009$, and type III can be separated from elastin, **$p<0.002$, wherein comparisons are done at 50 MHz and error bars denote standard deviations.
Figure 5C:
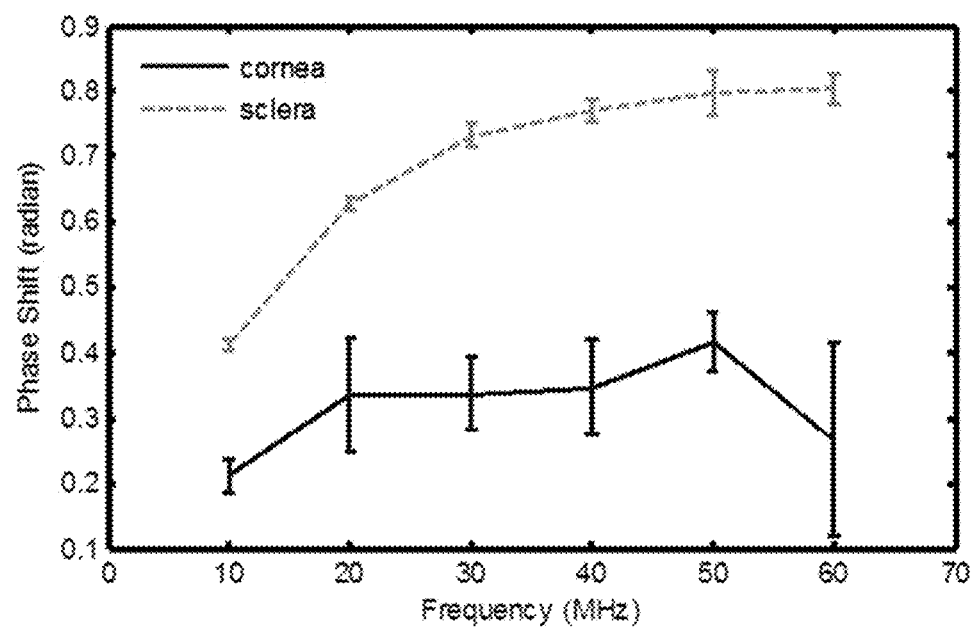
FIG. 5C is a graph showing that ocular cornea tissue have smaller phase shift than sclera tissue, *$p<0.0002$, wherein comparisons are done at 50 MHz and error bars denote standard deviations.
Figure 5D:
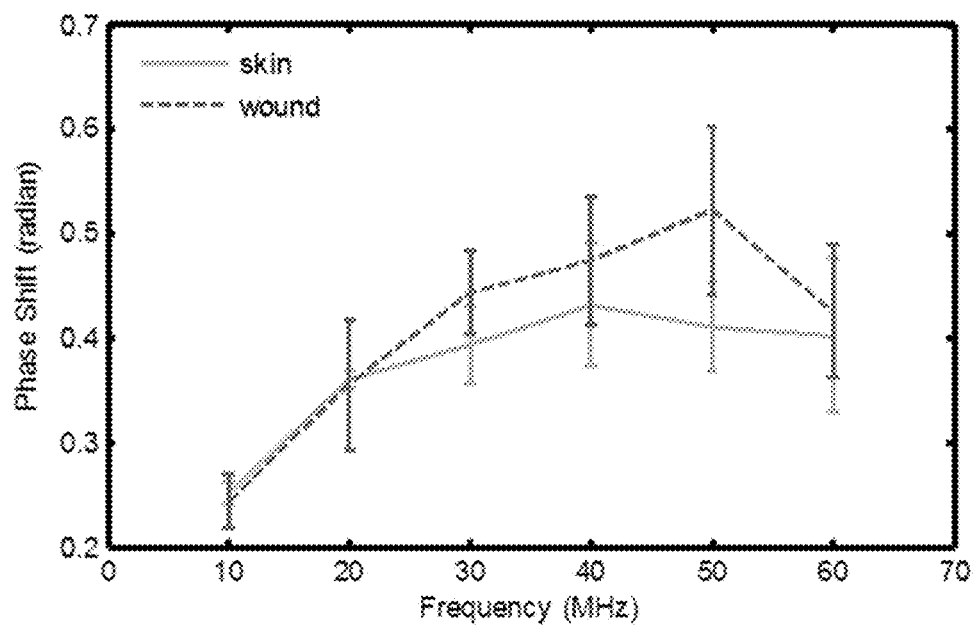
FIG. 5D is a graph showing that wound tissue have larger shifts compared to normal skin tissue, *$p<0.05$, wherein comparisons are done at 50 MHz and error bars denote standard deviations.

FIGS. 5A-5D show phase shifts of the tested samples, which indicates that these are consistent with lifetimes of fluorescence standards and can distinguish ECM proteins that comprise tissues. As seen in FIGS. 5A-5D, the phase shift angle rises with frequency as expected, following an inverse tangent profile consistent with equation (7). At a particular frequency, larger phase shift translates to longer lifetime. For the fluorescence standards, as shown in FIG. 5A, the phase shifts increased from FAD, fluorescein, to 9CA, in that order. For the proteins, as shown in FIG. 5B, collagen I consistently measures a smaller phase shift than collagen III at all frequencies, while elastin measures a larger phase shift than the collagen samples. For the bovine ocular tissues, as shown in FIG. 5C, the scleral tissue measures a much larger phase shift compared to corneal tissue. The cornea is critical to the optical functions of the eye's lens and its transparency is the result of uniform diameter and arrangement of its collagen fibers, whose crosslinking could be the cause of the smaller phase shift measurements. For the murine wound tissue, as shown in FIG. 5D, a larger phase shift is measured compared to normal skin tissue, which is indicative of longer lifetime components. Compared to the collagen measurements, this difference may be due to the deposition of collagen III (larger phase shift) in the wound during the healing process. It should be noted that multiple ECM proteins are present in the tissue samples, and collagen itself has multiple lifetime components. The multi-exponential decay model, described below, provides better fitting to extract lifetime information from these tissues.

Additionally the phase results show that the frequency band of 40-50 MHz has wide separations between collagen I and III, with tight standard deviations. Analysis of 50 MHz measurement, for example, gives a $p<0.009$ between collagen I and III, $p<0.002$ between collagen III and elastin. 50 MHz analysis also gives $p<0.0002$ between the ocular samples and $p<0.05$ between skin samples.

Frequency Domain Demodulation Results

Figure 6A:
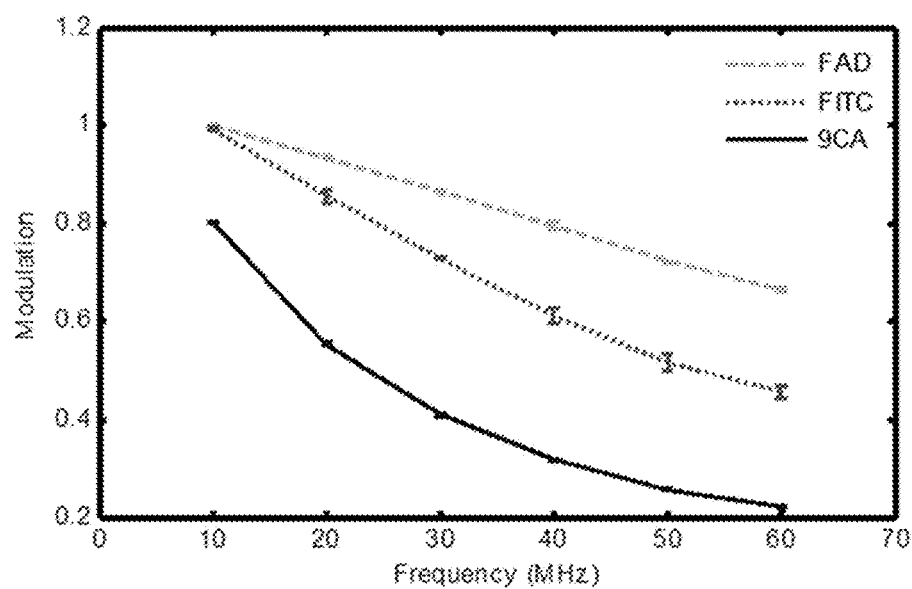
FIG. 6A is a graph showing that fluorescence standards show deeper demodulations between FAD, fluorescein, and 9CA, as expected by the order of their increasing lifetimes, wherein error bars denote standard deviations.
Figure 6B:
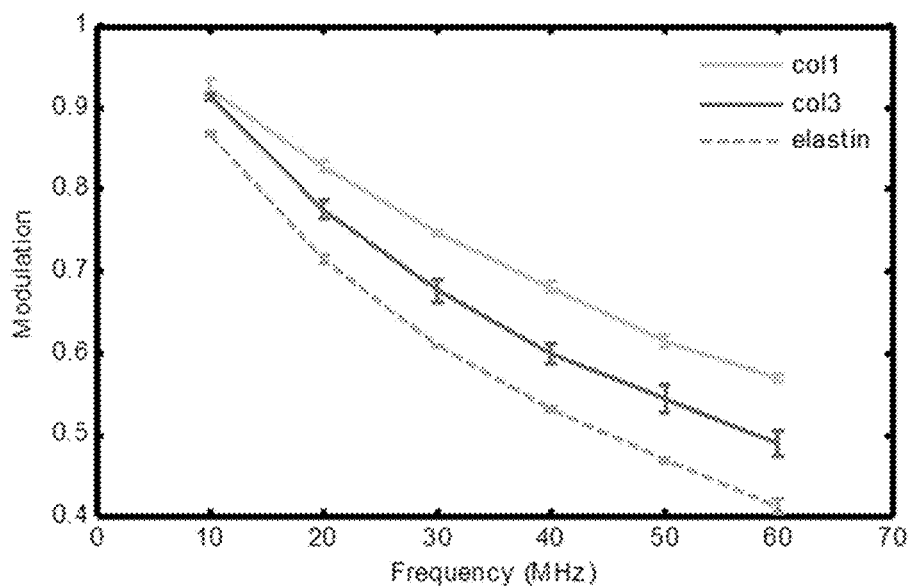
FIG. 6B is a graph showing that demodulation between type I and III collagen are distinct, $p<0.002$, and that type III can be separated from elastin, $p<0.001$, wherein comparisons are done at 50 MHz and error bars denote standard deviations.
Figure 6C:
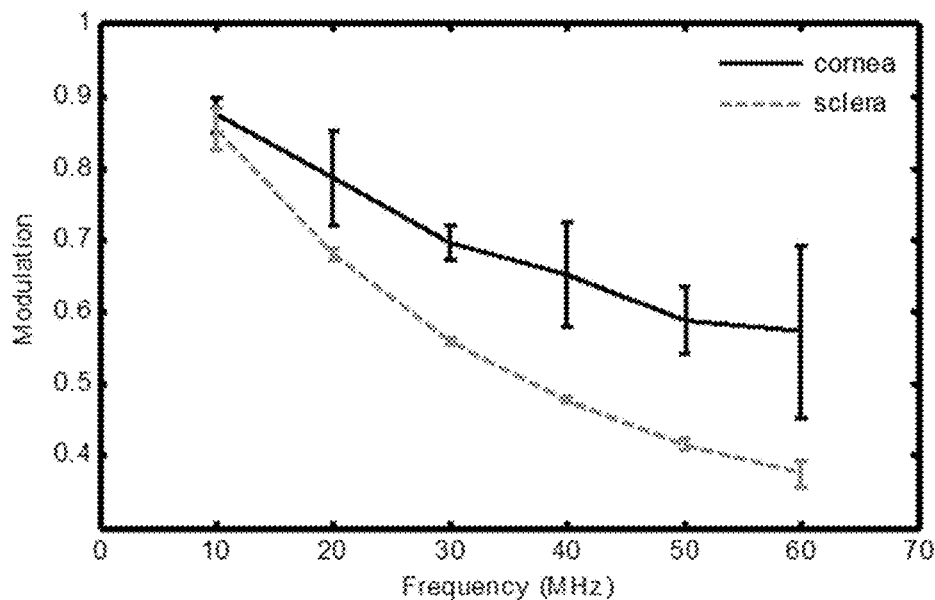
FIG. 6C is a graph showing that ocular cornea tissue have shallower apparent demodulation than sclera tissue, $p<0.002$, wherein comparisons are done at 50 MHz and error bars denote standard deviations.
Figure 6D:
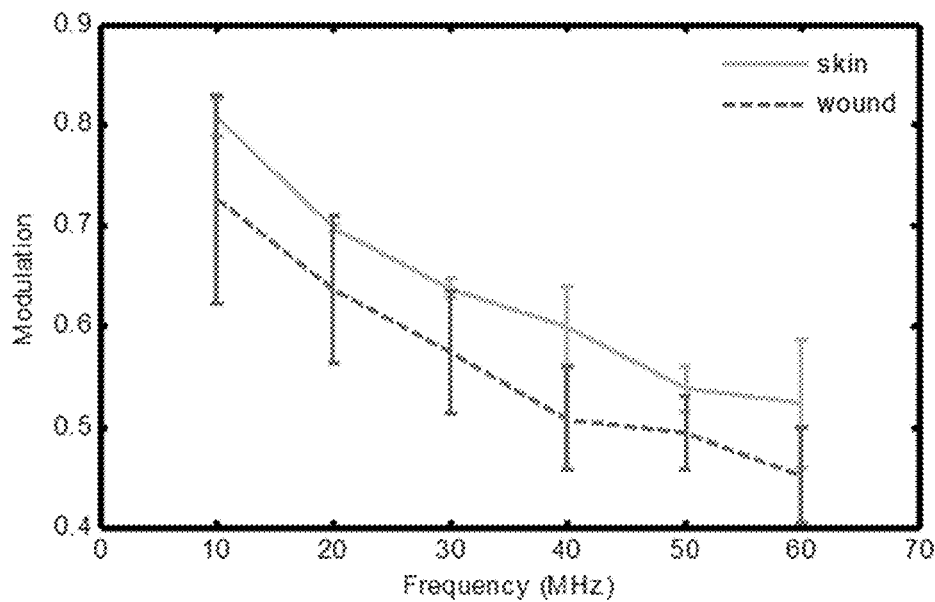
FIG. 6D is a graph showing that wound tissue have deeper demodulation compared to normal skin tissue, $p<0.07$, wherein comparisons are done at 50 MHz and error bars denote standard deviations.

Modulation values of the tested samples are given in FIGS. 6A-6D, which indicate that demodulation can distinguish collagen proteins from tissues. The demodulation ratios are seen to drop with frequency as expected, following a decay profile consistent with equation (8). At a particular frequency, deeper demodulation translates to longer lifetime. With reference to FIG. 6A, demodulation results from the standards followed that of the phase shift results putting FAD, fluorescein, and 9CA in order of increasing lifetimes. Again, with reference to FIG. 6B, collagen I versus III measured distinct demodulation ratios, both shallower than elastin's values. With reference to FIG. 6C, ocular tissue demodulation also agrees with the phase results, with sclera having deeper demodulation and thus longer lifetime than cornea tissue. With reference to FIG. 6D, the murine wound also exhibits deeper demodulation compared to normal skin tissue, which is consistent with the aforementioned premise that type III collagen is deposited into wound tissues during healing.

These demodulation results also show that the frequency band of 40-50 MHz has the best separation between collagen I and III. At 50 MHz, $p<0.002$ between collagen I and III and $p<0.001$ between collagen III and elastin. For the tissues, $p<0.002$ between the ocular samples and $p<0.07$ between skin samples, at that same frequency. These results indicate that data acquisition in the future can be simplified by focusing on 40-50 MHz bands. In the following section concerning a multi-exponential model, both the phase and demodulation results are combined in a minimizing function in order to calculate the combined lifetimes.

Multi-Exponential Fitting of Lifetimes Distinguishes Collagen Types

The phase shift and modulation results are fitted into single or multi-exponential decay models, and weighted with their respective standard deviations, by minimizing equation (9). The fitted lifetimes are shown in Tables 1-4. The lifetime fractional $\alpha$'s and $\tau$'s are shown along with their apparent $\tau_{avg}$ for each sample of standards, proteins, and tissues. A single exponential model is used to fit for the fluorescent standards. The fitting shows results of 2.57, 3.94, and 11.8 ns for FAD, fluorescein, and 9CA, respectively, which are comparable to known results. Protein samples are fitted to a two-exponential model, with a longer lifetime component and a shorter one around 1 ns, consistent with reported values. Collagen III's average lifetime is measured at 5.01 ns, distinct from and longer than the lifetime of collagen I, 3.95 ns, $p<0.001$. Other reports have also found longer lifetimes for collagen III compared to I. Elastin was distinct from type III collagen, $p<0.0002$, and measured the longest average lifetime of ECM proteins in this study, with a value of 6.78 ns.

TABLE 1

Single exponential fitting for fluorescence samples

| sample | Lifetimes (ns) $\tau_1$ | $\tau_2$ | Pre-exponential factors $\alpha_1$ | $\alpha_2$ | Fractional intensities $f_1$ | $f_2$ | Average lifetime (ns) $\tau_{avg}$ |
|---|---|---|---|---|---|---|---|
| FAD | 2.57 ± 0.02 | — | 1 | — | 1 | — | 2.57 ± 0.02 |
| FITC | 3.94 ± 0.05 | — | 1 | — | 1 | — | 3.94 ± 0.05 |
| 9CA | 11.75 ± 0.02 | — | 1 | — | 1 | — | 11.75 ± 0.02 |

TABLE 2

Multi-exponential fitting for protein samples

| sample | Lifetimes (ns) $\tau_1$ | $\tau_2$ | Pre-exponential factors $\alpha_1$ | $\alpha_2$ | Fractional intensities $f_1$ | $f_2$ | Average lifetime (ns) $\tau_{avg}$ |
|---|---|---|---|---|---|---|---|
| col1 | 6.77 ± 0.24 | 0.84 ± 0.04 | 0.121 | 0.879 | 0.525 | 0.475 | 3.95 ± 0.13* |
| col3 | 7.46 ± 0.24 | 0.76 ± 0.09 | 0.150 | 0.850 | 0.633 | 0.367 | 5.01 ± 0.22 |
| elastin | 9.37 ± 0.40 | 1.42 ± 0.20 | 0.238 | 0.762 | 0.673 | 0.327 | 6.78 ± 0.17** |

*collagen I vs. III p < 0.001,
**collagen III vs. elastin p < 0.0002

TABLE 3

Multi-exponential fitting for ocular tissue samples

| sample | Lifetimes (ns) $\tau_1$ | $\tau_2$ | Pre-exponential factors $\alpha_1$ | $\alpha_2$ | Fractional intensities $f_1$ | $f_2$ | Average lifetime (ns) $\tau_{avg}$ |
|---|---|---|---|---|---|---|---|
| cornea | 8.44 ± 0.82 | 0.22 ± 0.05 | 0.024 | 0.976 | 0.486 | 0.514 | 4.27 ± 0.84* |
| sclera | 9.53 ± 0.25 | 1.03 ± 0.09 | 0.254 | 0.746 | 0.759 | 0.241 | 7.48 ± 0.23 |

*cornea vs. sclera, p < 0.0015

TABLE 4

Multi-exponential fitting for wound skin samples

| sample | Lifetimes (ns) $\tau_1$ | $\tau T_2$ | Pre-exponential factors $\alpha_1$ | $\alpha_2$ | Fractional intensities $f_1$ | $f_2$ | Average lifetime (ns) $\tau_{avg}$ |
|---|---|---|---|---|---|---|---|
| skin | 13.08 ± 0.80 | 0.72 ± 0.14 | 0.049 | 0.951 | 0.484 | 0.516 | 6.72 ± 0.24* |
| wound | 18.98 ± 0.42 | 1.15 ± 0.32 | 0.052 | 0.948 | 0.475 | 0.525 | 9.74 ± 0.96 |

*skin vs. wound, p < 0.003

A two-exponential fitting is used for the tissue samples, follow by the calculation of $\tau_{avg}$. For the ocular tissues, cornea measurements show much shorter average lifetimes of 4.27 ns than sclera at 7.48 ns, p<0.0015. For the murine skin tissues, the 8 mm murine skin wound at 14 days post-wounding show a distinct, longer average lifetime at 9.74 ns versus normal skin at 6.72 ns, p<0.003. This difference is attributed to the bias of collagen III fibers (with longer lifetimes) laid down during the wound healing process. Murine wounds models used in this study have been reported to express high level of type III collagen around days 10-17 post wounding, coinciding with the day 14 sample in the present study.

Performance of FD Collagen Detection System

To provide a comparison of the temporal resolution and the sensitivity of the FD Collagen system, FIGS. 7A-7B show the lifetime standard deviations of repeat measurements of different sample amounts (FIG. 7A: collagen I mass; and FIG. 7B: FAD concentration), which correspond to a range of emission intensities. The sensitivity results show that the system can detect a minimum mass of 25 μg of type I collagen (FIG. 7A) and minimum concentration of 1 μM FAD (FIG. 7B), while maintaining below 5% relative standard deviation. These results mean that the signal is about 20 times higher than the measurement error itself. At these points, the detected optical power is about 3 nW, with a time resolution of about 200 ps. The probe illuminates a spot size of 5 mm, with skin penetration down to about 300 μm (365 nm light), which is equivalent to an excitation volume of 6 μL. Considering skin collagen composition to be about 70% by weight, in vivo measurements would involve about 4.1 mg using the probe. Two orders of magnitude finer sensitivity with 200 picosecond temporal resolution are achieved, adequate for resolving type I versus type III collagen.

Modifications for Complex Tissue ECM

As the ECM composition of ocular sclera, cornea, normal skin, and wound skin tissues are complex, the current multi-exponential model can benefit from an extra dimension of spectral resolution. First, the detection system is modified by focusing on the frequency band of 40-50 MHz, which simplifies data acquisition without sacrificing collagen differentiation, as shown herein. Also, instead of integrating all intensities above 400 nm, the emission is divided into 400-450 nm, 450-500 nm, and 500-550 nm, spectral bands using a simple filter wheel setup. These bands are biased towards collagen I, collagen III, and elastin lifetimes, respectively. This provides better discrimination using spectral-lifetime techniques reported by others, while still benefiting from the low-cost scheme of LED-based FD Collagen detection.

A low cost, low complexity LED-based tissue autofluorescence, FD Collagen system is described that is capable of measuring distinct lifetimes for type I and type III collagen and elastin. The phase shift and demodulation of the LED light source is calibrated at each scan frequency for both aqueous and solid samples. The measurements show that collagen samples are fitted to a two-exponential model, with type I collagen having shorter average lifetimes at 3.95 ns while type III at a longer 5.01 ns. The probe is tested on bovine ocular tissues, with cornea showing much shorter average lifetimes of 4.27 ns than sclera at 7.48 ns. Furthermore, measurements of 8 mm murine skin wound at 14 days post-wounding also show distinct, longer average lifetimes at 9.74 ns versus normal skin at 6.72 ns. Finally, the sensitivity results show two orders of magnitude lower detection limits than typical tissue and skin collagen compositions, with 200 picosecond lifetime resolutions. The system can be modified to focus on the 40-50 MHz frequency range while separating the emission into three wavelength bands, providing additional spectral-lifetime discriminations. The devices and methods provided herein specifically target and optimize frequency domain lifetime detection of collagen variants in tissue, via a compact, easy-to-use package aimed at enabling clinical wound monitoring, tissue biomechanics monitoring, and other non-invasive biomedical applications. These results and technique provide additional data points for collagen lifetimes in tissues, and further encourage clinical and interdisciplinary researches to use non-invasive optical biopsy for tissue monitoring.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for detecting a biological component in a subject, the method comprising:
    a. focusing sinusoidal modulated incident light from a light source on a biological sample;
    b. detecting a range of wavelengths of sinusoidal modulated fluorescent light emitted from a target biological component when present in the biological sample;
    c. determining greater than one frequency domain phase shift for the modulated fluorescent light and the modulated incident light;
    d. determining greater than one frequency domain amplitude modulation for the modulated fluorescent light; and
    e. determining greater than one frequency domain fluorescence lifetime of the biological component, so as to detect at least one of a presence and a quantity of the target biological component,
    wherein the determining the greater than one frequency domain fluorescence lifetime of the biological component comprises fitting the frequency domain phase shifts and the frequency domain amplitude modulations into a multi-exponential decay model.

2. The method according to claim 1, wherein focusing sinusoidal modulated incident light from a light source comprises focusing sinusoidal modulated incident light form a modulated light emitting diode (LED).

3. The method according to claim 1, wherein focusing sinusoidal modulated incident light from a light source comprises focusing light with a wavelength of 365 nm from a light emitting diode (LED) with a sinusoidal modulated intensity of from greater than or equal to about 10 MHz to less than or equal to about 100 MHz.

4. The method according to claim 3, wherein focusing light with a wavelength of 365 nm from an LED comprises focusing light with a sinusoidal modulated intensity of from greater than or equal to about 40 MHz to less than or equal to about 60 MHz through a 375 nm low-pass filter.

5. The method according to claim 1, wherein detecting a range of wavelengths of sinusoidal modulated fluorescent light comprises detecting a range of wavelengths of modulated fluorescent light with an avalanche photodiode.

6. The method according to claim 1, wherein focusing sinusoidal modulated incident light from a light source on a biological sample comprises focusing sinusoidal modulated incident light from a light source on the subject's skin.

7. The method according to claim 1, wherein the biological component is selected from the group consisting of collagen type I, collagen type III, elastin, and combinations thereof.

8. A method for detecting a combination of tissue structural proteins in a biological sample, the method comprising:
    a. detecting a range of sinusoidal fluorescent light emitted from a combination of tissue structural proteins when present in a biological sample;
    b. determining greater than one frequency domain phase shift value and greater than one frequency domain amplitude suppression value for the range of sinusoidal fluorescent light emitted from the combination of tissue structural proteins;
    c. fitting the greater than one frequency domain phase shift value and the greater than one frequency domain amplitude suppression value for the range of sinusoidal fluorescent light emitted from the combination of tissue structural proteins into a multi-exponential decay model; and
    d. determining frequency domain fluorescence lifetimes of the combination of tissue structural proteins so as to detect their presence in the biological sample.

9. The method according to claim 8, further comprising, prior to the detecting a range of sinusoidal fluorescent light, focusing incident light with a wavelength of from greater than or equal to about 350 nm to less than or equal to about 375 nm and a sinusoidal modulated intensity of from greater than or equal to about 40 MHz to less than or equal to about 60 MHz from a light emitting diode (LED) on the biological sample.

10. The method according to claim 9, wherein the biological sample is skin of a mammalian sample and focusing incident light on the skin of the mammalian subject includes focusing incident light on a wound located on the skin of the mammalian subject.

11. The method according to claim 9, wherein focusing incident light on the biological sample comprises focusing light from the LED through a first convex lens, through a 275 nm-375 nm bandpass excitation filter, through a second convex lens, and through a fiber optic probe.

12. The method according to claim 8, wherein the combination of tissue structural proteins includes type I collagen, type III collagen, and elastin.

13. The method according to claim 12, wherein the method further comprises:
comparing the frequency domain fluorescence lifetime of the elastin to the frequency domain fluorescence lifetimes of the type I collagen and type III collagen and determining a quantity of the elastin relative to the type I collagen and type III collagen.

14. The method according to claim 8, wherein detecting comprises illuminating a plurality of optical fibers with the sinusoidal fluorescent light emitted from the combination of tissue structural proteins, focusing the light through a convex lens, through one or more filters, through an aspherical lens, and onto an avalanche diode.

15. The method according to claim 8, further comprising:
determining relative quantities of the combination of tissue structural proteins in the biological sample from the frequency domain fluorescence lifetimes.

16. A device for measuring an analyte in a biological sample by frequency domain fluorescence lifetime spectroscopy, the device comprising:
 a. a modulated light emitting diode (LED) source;
 b. a first focusing component;
 c. a focusing optical fiber;
 d. a detecting optical fiber;
 e. a second focusing component; and
 f. an avalanche detector,
 wherein the first focusing component focuses light from the LED source into the focusing optical fiber towards the biological sample, and the detecting optical fiber captures fluorescent light emitted from the analyte in the biological sample and directs the fluorescent light to the second focusing component that focuses the fluorescent light into the avalanche detector.

17. The device according to claim 16, wherein the LED source emits light with a wavelength of from about 350 nm to about 375 nm with a sinusoidal modulated intensity of from about 40 MHz to about 60 MHz.

18. The device according to claim 16, wherein the first focusing component comprises a 275-375 bandpass filter positioned between first and second plano convex lenses.

19. The device according to claim 16, wherein the device comprises a plurality of detecting optical fibers.

20. The device according to claim 16, further comprising a probe through which modulated light from the focusing optical fiber is focused onto the biological sample and through which fluorescent light emitted from the analyte in the biological sample is captured and transferred to the detecting optical fiber.

* * * * *